US009603551B2

(12) United States Patent
Lamesch

(10) Patent No.: US 9,603,551 B2
(45) Date of Patent: Mar. 28, 2017

(54) INDUCTIVE RESPIRATION SENSOR

(71) Applicant: IEE International Electronics & Engineering S.A., Echternach (LU)

(72) Inventor: Laurent Lamesch, Reichlange (LU)

(73) Assignee: IEE International Electronics & Engineering S.A., Echternach (LU)

( * ) Notice: Subject to any disclaimer, the term of this patent is extended or adjusted under 35 U.S.C. 154(b) by 0 days.

(21) Appl. No.: 14/914,604

(22) PCT Filed: Aug. 18, 2014

(86) PCT No.: PCT/EP2014/067581
§ 371 (c)(1),
(2) Date: Feb. 25, 2016

(87) PCT Pub. No.: WO2015/028335
PCT Pub. Date: Mar. 5, 2015

(65) Prior Publication Data
US 2016/0198979 A1    Jul. 14, 2016

(30) Foreign Application Priority Data

Aug. 28, 2013    (LU) .......................................... 92272

(51) Int. Cl.
*H03F 3/08*    (2006.01)
*A61B 5/08*    (2006.01)
(Continued)

(52) U.S. Cl.
CPC ............ *A61B 5/0809* (2013.01); *A61B 5/725* (2013.01); *H03F 3/45475* (2013.01);
(Continued)

(58) Field of Classification Search
CPC ....... A61B 5/08; A61B 5/0806; A61B 5/0809; A61B 5/0816; H03F 3/08; H03F 3/04
(Continued)

(56) References Cited

U.S. PATENT DOCUMENTS 3,206,692 A * 9/1965 Fogle .................. H01L 27/0658
257/539
4,065,668 A * 12/1977 Monticelli ................ H03F 3/08
250/214 P
(Continued)

FOREIGN PATENT DOCUMENTS

| EP | 0509272 A1 | 10/1992 |
| GB | 1596298 A | 8/1981 |
| WO | 2010131267 A1 | 11/2010 |

OTHER PUBLICATIONS

International Search report issued Nov. 4, 2014 re: Application No. PCT/EP2014/067581; pp. 1-5; citing: US 2008/183095 A1, GB 1 596 298 A, WO 2010/131267 A1, US 2010/172657 A1, EP 0 509 272 A1 and US 2008/232822 A1.
(Continued)

*Primary Examiner* — Henry Choe
(74) *Attorney, Agent, or Firm* — Reising Ethington P.C.

(57) ABSTRACT

An inductive respiration sensor (10) comprises an inductive transducer (12) and sensing circuitry. The sensing circuitry comprises a transimpedance amplifier, TIA, (14), the sense input (16) of which is operatively connected to the inductive transducer. The TIA is configured to drive a current from its output (20) into the sense input such that the voltage on the sense input follows the voltage applied to the reference input (18) and to cause a voltage on the output indicative of the current. The TIA comprises a first (34) and a second (30) transistor. The collector or drain and the emitter or source of the first transistor are operatively connected between the sense input and the output of the TIA. The emitter or source of the second transistor is connected to the reference input, the collector or drain of the second transistor is connected to the base or gate of the first transistor, and the base or gate of the second transistor is connected to the sense input.

11 Claims, 4 Drawing Sheets

(51) Int. Cl.
*A61B 5/00* (2006.01)
*H03F 3/45* (2006.01)

(52) U.S. Cl.
CPC ............... *H03F 2200/261* (2013.01); *H03F 2203/45544* (2013.01); *H03F 2203/45594* (2013.01)

(58) Field of Classification Search
USPC ..................................... 330/174, 288, 308
See application file for complete search history.

(56) References Cited

U.S. PATENT DOCUMENTS

| | | | |
|---|---|---|---|
| 5,913,830 A | | 6/1999 | Miles |
| 5,936,231 A | * | 8/1999 | Michiyama ............... G01J 1/44 250/214 A |
| 8,493,154 B1 | * | 7/2013 | Camargo ............... H03F 1/223 330/296 |
| 8,928,412 B2 | * | 1/2015 | Liou ..................... H03F 1/302 330/285 |
| 2008/0183095 A1 | | 7/2008 | Austin et al. |
| 2008/0232822 A1 | | 9/2008 | Furudate et al. |
| 2010/0172657 A1 | | 7/2010 | Uesaka |

OTHER PUBLICATIONS

Written Opinion issued Nov. 4, 2014 re: Application No. PCT/EP2014/067581; pp. 1-5; citing: US 2008/183095 A1, GB 1 596 298 A, WO 2010/131267 A1, US 2010/172657 A1, EP 0 509 272 A1 and US 2008/232822 A1.

* cited by examiner

INDUCTIVE RESPIRATION SENSOR

TECHNICAL FIELD

The present invention generally relates to an inductive sensor, in particular for sensing respiration parameters (e.g. frequency and volume) of a subject.

BACKGROUND ART

U.S. Pat. No. 5,913,830 discloses an inductive plethysmography respiration sensor for measuring the change of circumference and cross-sectional area of the chest or abdomen. The sensor includes a conductor loop with ("inactive") sections in which the conductor runs parallel to the direction in which the sensor expands and contracts when the person wearing it breathes and ("active") sections in which the conductor comprises a sharp bend in the transversal direction. When the sensor is stretched, the bends change shape, leading to a change in inductance of the conductor loop.

Whereas U.S. Pat. No. 5,913,830 fails to disclose any details about the sensing circuitry, two types of circuits are conventionally used for measuring inductance changes. The first type of circuit is an LC oscillator that uses the sensing coil as tank element. The oscillator frequency is indicative of the inductance. This circuit has the disadvantage that the LC oscillator may lock its frequency to an external magnetic field with a frequency close to the tank frequency. This could happen, for example, when two persons wearing the same measurement device are close to each other, or when an electromagnetic field is present which is generated by a for example a radio transmitter operating at a frequency close to the resonance of the LC oscillator. The second type of circuit uses a voltage divider driven by a high-frequency periodic signal (e.g. at 1 MHz). The voltage divider comprises a reference impedance and the inductive element. The amplitude of the divider output voltage is indicative of the inductance. An inductive sensor has typically an inductance of about 1 µH and a variation of up to 100 nH when the subject is breathing. At a frequency of 1 MHz, an inductance of 100 nH corresponds to an impedance of 0.628 Ω. This implies that in order to extract a measurable signal, either a large current must be used to generate a usable divider output voltage, conflicting with the low power requirement, or a very small output voltage must be amplified, conflicting with the low power and low cost requirements, or a higher operating frequency must be employed, which conflicts with the low power requirement.

BRIEF SUMMARY

The invention provides an improved inductive respiration sensor.

In accordance with the invention, an inductive respiration sensor comprises an inductive transducer configured to produce a variable inductance when subjected to mechanical deformation (caused by breathing) and sensing circuitry. The sensing circuitry comprises a transimpedance amplifier having a reference input, a sense input and an output. The sense input is operatively connected to the inductive transducer and the transimpedance amplifier is configured to drive a current from the output into the sense input such that the voltage on the sense input follows the voltage applied to the reference input and to cause a voltage on the output indicative of the current. Specifically, the transimpedance amplifier comprises a first transistor and a second transistor. The first transistor comprises a first connection (a collector or drain), a second connection (an emitter or source) and a third connection (a base or gate), the first and second connections of the first transistor being operatively connected between the sense input and the output of the transimpedance amplifier. The second transistor also comprises a first connection (a collector or drain), a second connection (an emitter or source) and a third connection (a base or gate), the second connection of the second transistor being connected to the reference input, the first connection of the second transistor being connected to the third connection of the first transistor, and the third connection of the second transistor being connected to the sense input. In what follows, the term "first connection" designates a collector or drain, the term "second connection" an emitter or source and the term "third connection" a base or gate, depending on whether the transistor considered is a bipolar junction transistor or a field-effect transistor.

As those skilled in the art will appreciate, the first and second transistors form together a negative feedback control loop, in which the first transistor is the actuator and the second transistor takes the role of the controller. In case of bipolar junction transistors, the base-emitter voltage difference of the second transistor controls the collector-emitter current across the second transistor. At the collector, this translates into a voltage, which is applied to the base of the first transistor and controls the first transistor such that the voltage on the sense input is drawn toward the voltage of the reference input. In case of field-effect transistors, the function is similar, except that the base, emitter and collector terminals are replaced by the gate, source and drain terminals.

The advantage of the feedback loop with the first and second transistors compared to a solution with one transistor having the reference voltage applied on its base is that the input impedance is greatly reduced (by a factor approximately equal to the current gain of the second transistor). Compared to the above-mentioned voltage divider method, the voltage resulting on the output of the transimpedance amplifier needs no high-gain amplification, which leads to lower power requirements and potentially lower production costs.

Preferably, the inductive transducer is AC-coupled to the sense input by a coupling capacitor in order to prevent direct current from flowing across the inductive transducer. The coupling capacitor could also be arranged in series with the inductive transducer.

According to a preferred embodiment of the invention, the inductive respiration sensor comprises a signal generator operatively connected to the reference input, the signal generator being configured to apply an alternating voltage (e.g. with a frequency comprised in the range from 10 kHz to 100 MHz, preferably from 10 kHz to 1 MHz) to the reference input. The signal generator could e.g. comprise a low-pass filter connected to a digital signal output of a microcontroller producing a square wave. In this case, the cutoff frequency of the filter is preferably selected such that the filter suppresses the harmonics of the fundamental frequency, producing a sine wave at its output.

Preferably, the inductive respiration sensor comprises a synchronous rectifier operatively connected to the output of the transimpedance amplifier for converting the alternating voltage into a direct voltage indicative of the impedance or the inductance.

The signal generator preferably comprises a transistor matched to the second transistor, the emitter or source of the matched transistor being connected with the second connection of the second transistor. By using matched bipolar junction transistors, the forward base-emitter junction voltage of the second transistor is compensated. The same compensation technique can be used for compensating the gate-source voltage when employing matched MOSFETs instead.

According to a preferred embodiment of the invention, the transimpedance amplifier, hereinafter termed first transimpedance amplifier, is operatively connected to the inductive transducer at a first terminal thereof and the inductive respiration sensor comprises a second transimpedance amplifier with a reference input, a sense input and an output, the sense input of the second transimpedance amplifier being operatively connected to the inductive transducer at a second terminal thereof. The second transimpedance amplifier is configured to drive a current from the output of the second transimpedance amplifier into the sense input of the second transimpedance amplifier such that such that the voltage on the sense input of the second transimpedance amplifier follows a voltage applied to the reference input of the second transimpedance amplifier and to cause a voltage on the output of the second transimpedance amplifier indicative of the current. The second transimpedance amplifier comprises, in particular, a third transistor and a fourth transistor. The third transistor comprises first connection, a second connection and a third connection, the first and second connections of the third transistor being operatively connected between the sense input of the second transimpedance amplifier and the output of the second transimpedance amplifier. The fourth transistor also comprises first connection, a second connection and a third connection, the second connection of the fourth transistor being connected to the reference input of the second transimpedance amplifier, the first connection of the fourth transistor being connected to the third connection of the third transistor, and the third connection of the fourth transistor being connected to the sense input of the second transimpedance amplifier.

In this embodiment, the inductive transducer may be operated in differential mode. Preferably, this is achieved using a signal generator operatively connected to the reference input of the first transimpedance amplifier and with opposite polarity to the reference input of the second transimpedance amplifier, the signal generator being thus configured to generate an alternating voltage difference between the reference inputs of the first and second transimpedance amplifiers.

The signal generator may comprise a low-pass filter connected to a digital signal output of a microcontroller.

The inductive respiration sensor may comprise a synchronous rectifier operatively connected, e.g. via a multiplexer or switch, to the output of the first transimpedance amplifier and to the output of the second transimpedance amplifier.

Preferably, a fifth transistor matched to the second transistor and a sixth transistor matched to the fourth transistor are provided, the emitter or source of the fifth transistor being connected with the second connection of the second transistor and the emitter or source of the sixth transistor being connected with the second connection of the fourth transistor in order to compensate the forward base-emitter junction voltage or the gate-source voltage of the second and fourth transistors.

BRIEF DESCRIPTION OF THE DRAWINGS

Further details and advantages of the present invention will be apparent from the following detailed description of several not limiting embodiments with reference to the attached drawings, wherein.

DESCRIPTION OF PREFERRED EMBODIMENTS

Figure 1:
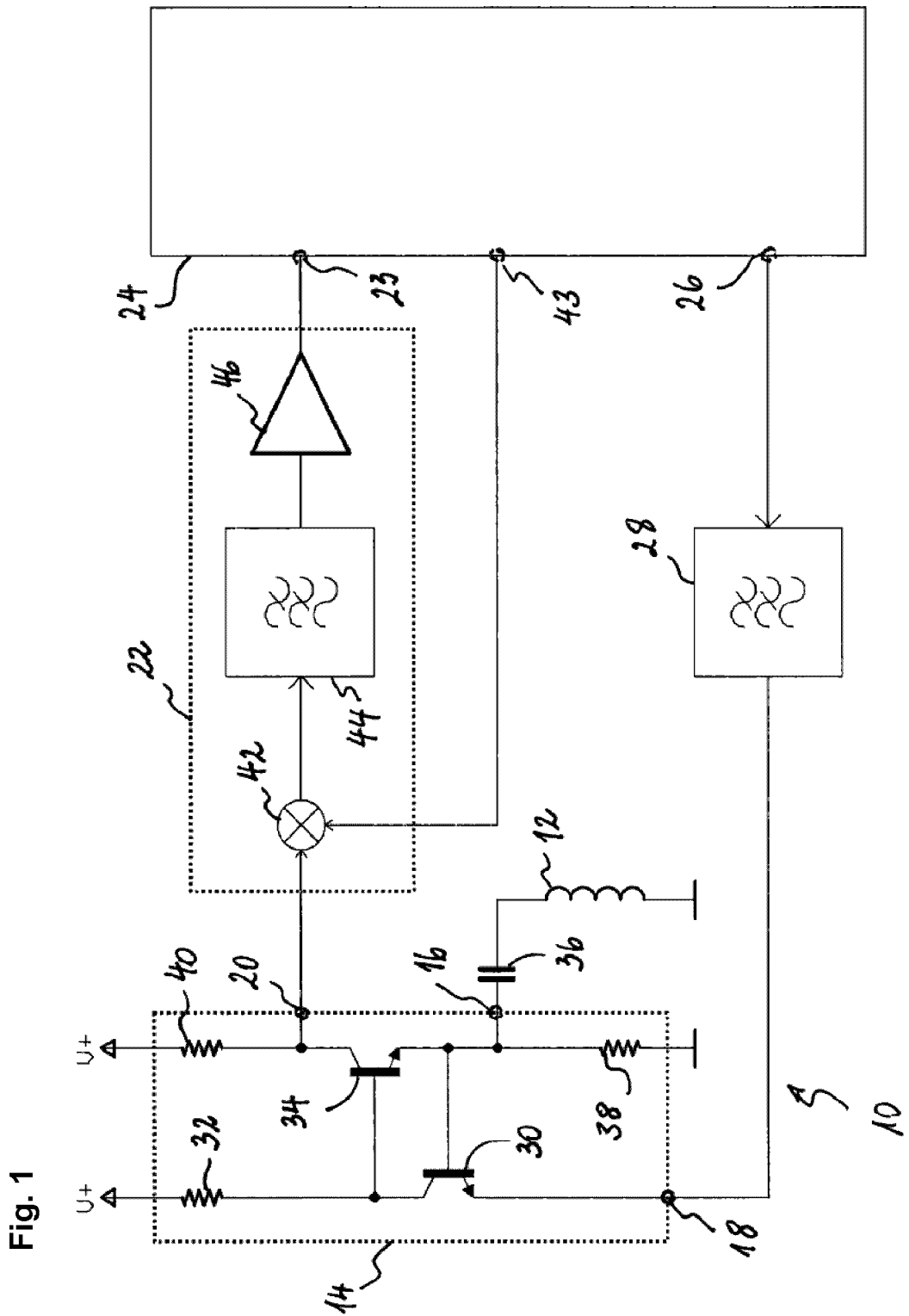
FIG. 1 is a block schematic diagram of an inductive respiration sensor according to a first preferred embodiment of the invention.

FIG. 1 shows a block schematic diagram of an inductive respiration sensor 10 according to a preferred embodiment of the invention. The respiration sensor 10 comprises an inductive transducer 12 having an inductance that varies when the inductive transducer 12 is mechanically deformed. The inductive transducer 12 can e.g. be a conductor loop with variable loop area, a coil or the like. The inductive transducer 12 is connected to the sense input 16 of transimpedance amplifier 14. When the respiration sensor is operating, the transimpedance amplifier 14 drives a current into the sense input 16 such that the voltage on the sense input follows the alternating reference voltage applied to the reference input 18 of the transimpedance amplifier 14. The alternating voltage thereby resulting on the output 20 of the transimpedance amplifier is indicative of the current flowing into the sense input 16. The alternating output voltage is converted into a direct voltage by the synchronous rectifier 22. The rectified signal is input into an analog signal input 23 of microcontroller 24, which is configured to convert the analog signal into a digital signal and to carry out the evaluations (e.g. determination of breathing rate, respiration volume, etc.)

The microcontroller 24 generates a square wave at its square wave output 26, of a frequency preferably in the range between 10 kHz and 1 MHz. Low-pass filter 28 transforms the square wave into a sine wave, while at the same time attenuating the amplitude to a value in the range between 10 mV and 100 mV. The resulting sine wave voltage is applied to the reference input of the transimpedance amplifier, which is tied to the emitter of transistor 30. Transistor 30 amplifies the voltage between its base and emitter and generates a collector current indicative of that voltage difference. The collector of transistor 30 is connected to the voltage supply via resistor 32. Accordingly, the current drawn across the collector-emitter path of transistor 30 results in a corresponding voltage on the collector, which is applied to the base of transistor 34. The emitter voltage of transistor 34, i.e. the voltage on the sense input 16, follows the voltage at the base of transistor 34. The emitter voltage is applied to the base of transistor 30, whereby the feedback loop made of transistors 30 and 34 is closed. The feedback loop keeps the voltage at the emitter of transistor 34 substantially equal, in terms of amplitude and phase, to the emitter voltage of transistor 30.

The alternating voltage at the sense input 16 is applied to the inductive transducer 12 via a coupling capacitor 36. The impedance of capacitor 36 is selected substantially smaller than the impedance of inductive transducer 12 at the operating frequency. With an inductance of about 1 µH of the inductive transducer and an operating frequency of 1 MHz, a capacitance of 1 µF may e.g. be used.

Resistor 38 sets the DC bias current of transistor 34 and is selected with an impedance larger than the impedance of inductive transducer 12 at the operating frequency. Due to the feedback loop, the alternating voltage across the series connection of the inductive transducer 12 and the coupling capacitor 36 is substantially equal to the alternating voltage at the output of filter 28. The AC current flowing into the emitter of transistor 34 is, therefore, substantially defined by the inductance of inductive transducer 12 and the AC voltage on the output of filter 28. Substantially the same AC current flows out of the collector of transistor 34. The error due to finite current gain of transistor 34 can be neglected in this application. Due to the resistor 40, the AC current results in a proportional AC voltage (measurement voltage) on the output 20 of the transimpedance amplifier 14.

The output AC voltage is then converted into a DC voltage with synchronous rectifier 22. The mixer 42 mixes the measurement voltage with a square wave provided at output 43 of microcontroller 24. This square wave has the same frequency as the square wave provided at output 26, but the microcontroller 24 is configured to modify the phase difference between the square waves. The mixed signal is fed to low-pass filter 44, which removes high-frequency components and passes the resulting DC voltage through DC amplifier 46 to the ADC input 23 of microcontroller 24. The gain of amplifier 46 can be appreciably smaller compared to the gain of an amplifier that would be required when using the voltage divider method mentioned above.

The microcontroller can determine the reactive part of the complex impedance between the sense input 16 and ground by measuring the imaginary part of the complex current across the collector of transistor 34. This is achieved by imposing a 90°-phase-shift of the square wave controlling the mixer 42 with respect to the sine wave applied to the reference input of the transimpedance amplifier 14. Similarly, the resistive part of the of the complex impedance between the sense input 16 and ground can be determined by measuring the real part of the complex current across the collector of transistor 34. In this case, the microcontroller imposes a 0°-phase-shift of the square wave controlling the mixer 42 with respect to the sine wave applied to the reference input of the transimpedance amplifier 14. The complex impedance between the sense input 16 and ground is obtained by combining the resistive and the reactive parts.

In an example configuration, the parameters were chosen as follows: 500Ω for resistor 38, 1000Ω for resistor 40 and 6000Ω for resistor 32, the transistors 30 and 34 were of type 2N3904, and the supply voltage was chosen $V_+$=3 V.

The advantage of the feedback loop with transistors 34 and 30 is that the input impedance of the transimpedance amplifier is greatly reduced compared to a configuration in which transistor 30 and resistor 32 are omitted and the AC reference voltage is applied to the base of transistor 34. Without the feedback loop, when operating transistor 34 with a DC current of 1.2 mA for example, the input impedance is approximately 27 mV/1.2 mA=22.5Ω. This input resistance would form, together with the variable impedance of the inductive sensor of 0.628Ω (assuming an inductance variation of 100 nH and an operating frequency of 1 MHz), a voltage divider, resulting in a signal loss of a factor 43. With the feedback loop, i.e. in the situation of FIG. 1, the input resistance of the transimpedance amplifier 14 is decreased approximately by a factor equal to the current gain of transistor 30, which is typically 100 for a type 2N3904 transistor. The improved input resistance thus amounts only to approximately 0.225Ω.

Figure 2:
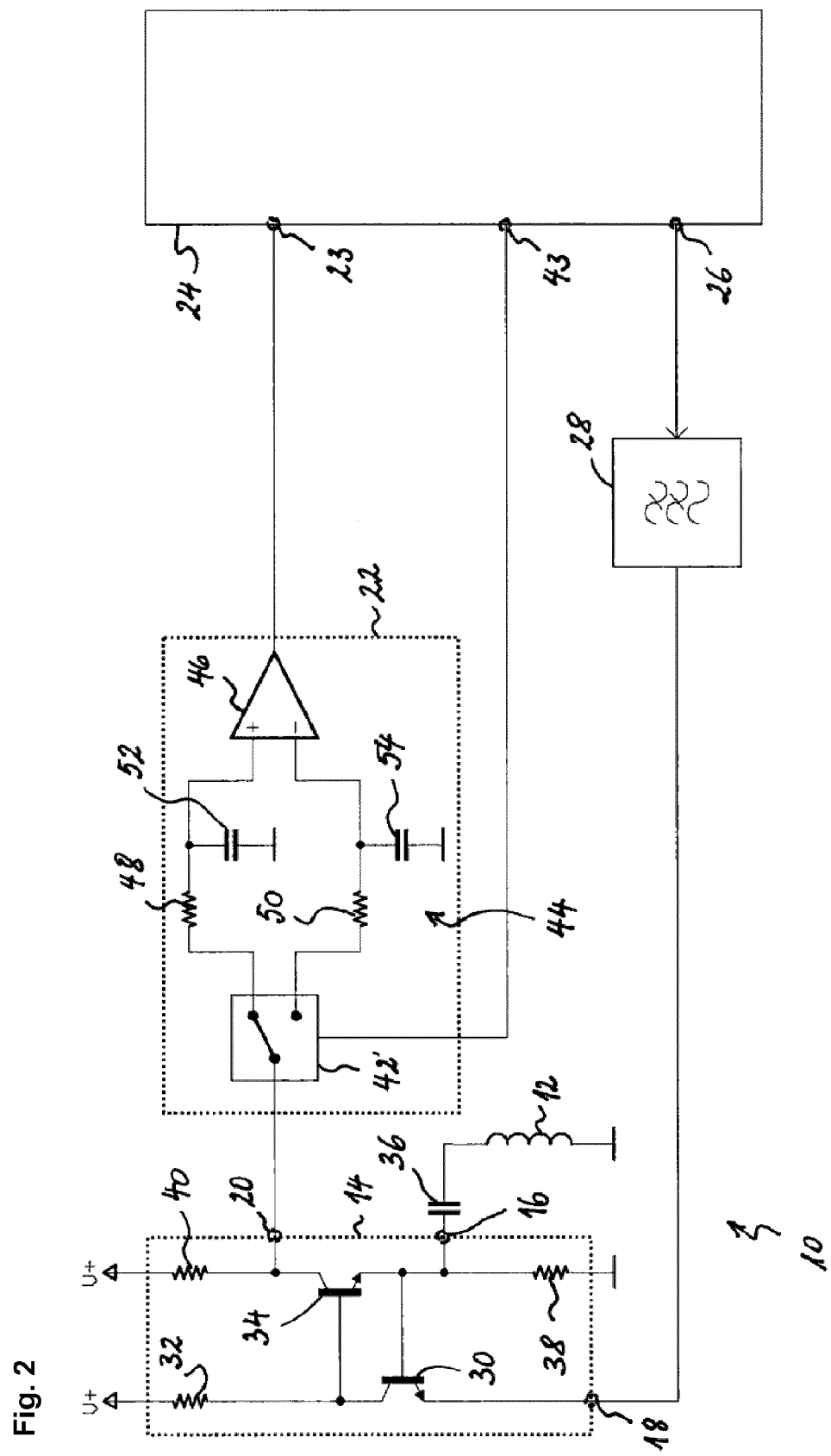
FIG. 2 is a block schematic diagram of a preferred implementation of the inductive respiration sensor of FIG. 1.

FIG. 2 illustrates a preferred implementation of the embodiment of FIG. 1. Specifically, FIG. 2 illustrates an example implementation of the synchronous rectifier 22. The mixing function of mixer 42 is taken over by multiplexer 42', which alternately switches the measurement voltage between the inverting input and the non-inverting input of difference amplifier 46. The low-pass filter 44 comprises a resistor 48, 50 and a capacitor 52, 54, forming an RC filter in each branch. Difference amplifier 46 amplifies the difference of the low-pass filters and passes the resulting DC voltage to ADC input 23.

Figure 3:
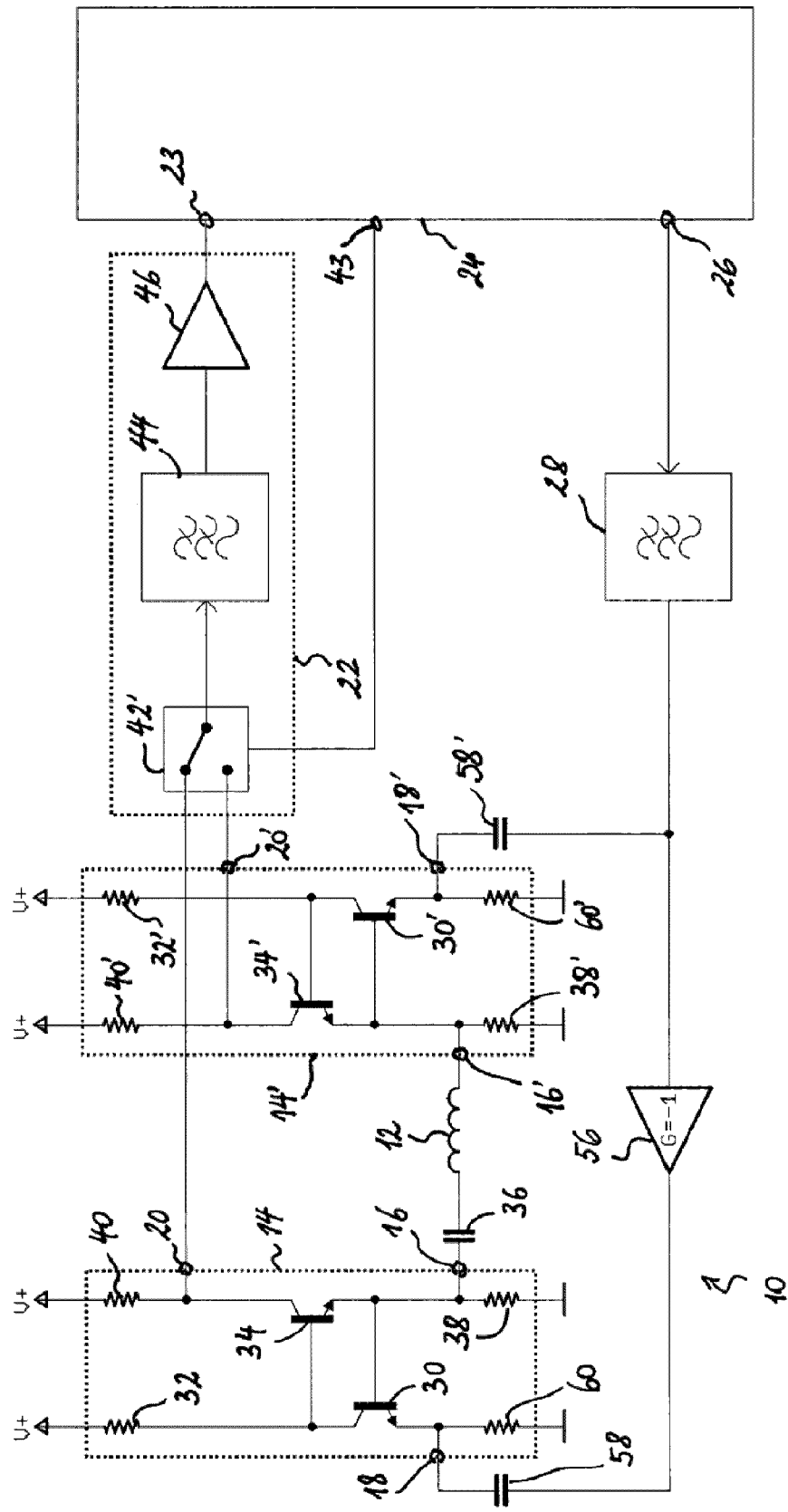
FIG. 3 is a block schematic diagram of an inductive respiration sensor according to a second preferred embodiment of the invention.

FIG. 3 shows another preferred embodiment of an inductive respiration sensor. The circuit in FIG. 1 is duplicated, and the impedance of the inductive transducer 12, connected between the sense inputs 16, 16' of the transimpedance amplifiers 14, 14', is measured in a differential way. This has the advantage that common mode noise entering the circuit via the inductive transducer 12 or the transducer cabling is substantially attenuated.

The first and second transimpedance amplifiers 14 and 14' are of the same configuration. In FIG. 3, components of transimpedance amplifier 14 have thus been given the same reference number as their identical counterpart in transimpedance amplifier 14, followed by a "prime" symbol (') for proper distinction. For a detailed description of the configuration of the transimpedance amplifiers 14 and 14', the reader may thus refer to FIG. 1 and the corresponding explanations.

In the embodiment illustrated in FIG. 3, the sine wave output by low-pass filter 28 is fed with opposite polarity to the reference inputs 18 and 18' of the transimpedance amplifiers 14 and 14'. Inverting amplifier 56 inverts the sine wave output by low-pass filter 28. The inverted copy of the sine wave is coupled to the reference input 18 of transimpedance amplifier 14 with capacitor 58 and resistor 60, whereas the non-inverted copy of the sine wave is coupled to the reference input 18' of transimpedance amplifier 14' with capacitor 58' and resistor 60'. Capacitors 58 and 58' are substantially identical. The same is true for resistors 60 and 60'. Due to the feedback loops, the voltage on the sense input 16 is substantially equal to the inverted output of the low-pass filter 28, and the voltage on the sense input 16' is substantially equal to the output of low-pass filter 28. The voltage difference between the collectors of transistors 34 and 34' is synchronously rectified by the synchronous rectifier 22.

Figure 4:
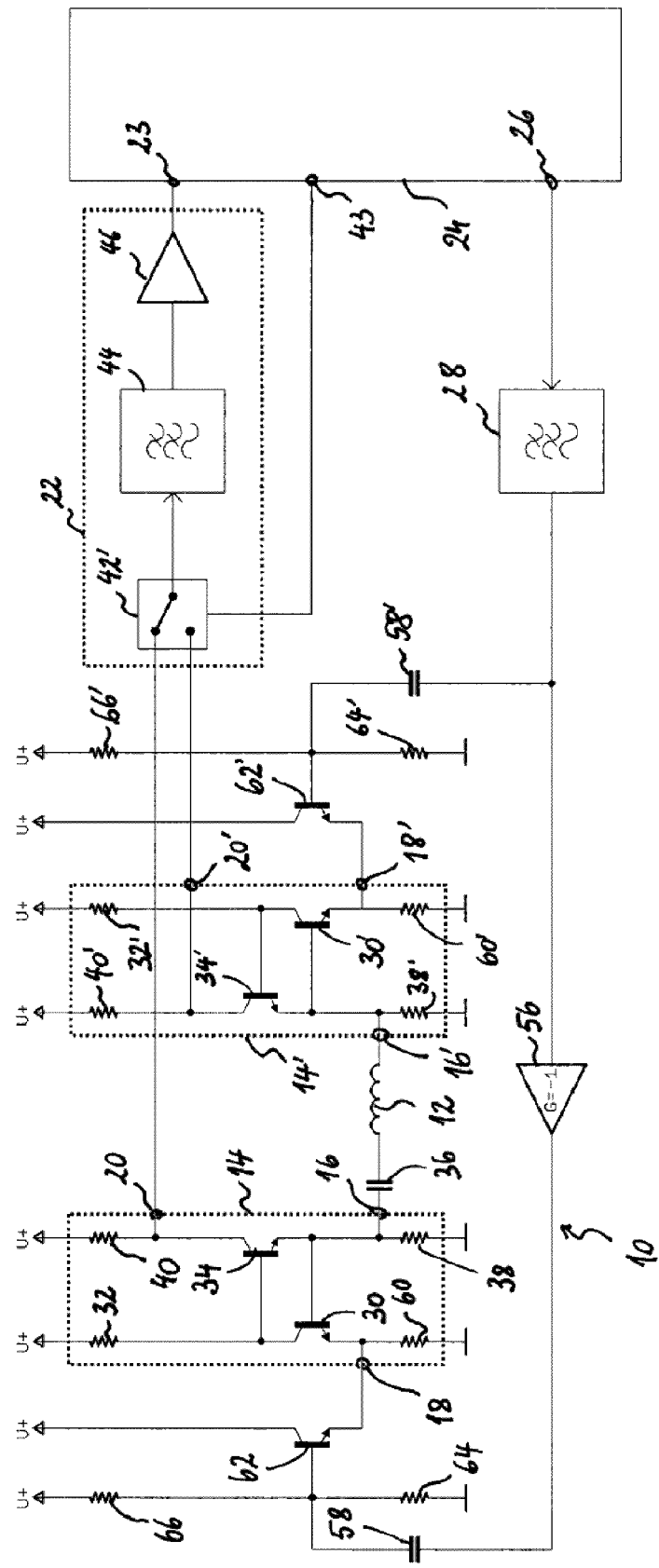
FIG. 4 is a block schematic diagram of an inductive respiration sensor according to a third preferred embodiment of the invention.

Yet another preferred embodiment of an inductive respiration sensor is shown in FIG. 4. The circuits illustrated in FIGS. 1 to 3 have the disadvantage that the DC bias currents of transistors 34, 34' depend on the forward BE junction voltage of transistors 30 and 30' respectively. The circuit in FIG. 4 solves this problem using the additional transistors 62 and 62' and bias resistors 64, 64', 66, 66'. Transistors 30 and 62 form a first matched transistor pair and transistors 30' and 62' form a second matched transistor pair. Resistors 64 and 66 define the DC bias voltage at the base of transistor 62. The DC bias emitter voltage of transistor 62 equals the DC bias base voltage minus the forward BE junction voltage of transistor 62. The DC bias base voltage of transistor 30 equals the DC bias emitter voltage of transistor 30 plus forward BE junction voltage of transistor 30. By using matched transistors for transistor 30 and 62, the DC bias base voltage of transistor 30 results in being substantially equal to the DC bias base voltage of transistor 62, which is defined by the supply voltage ($V_+$) and resistors 64 and 66. The DC bias current of transistor 34 is thus defined by the DC bias base voltage of transistor 30 divided by the resistance of resistor 38. Accordingly, the DC bias current of transistor 34 is defined by the supply voltage, resistances 64, 66 and 38. The DC bias current of transistor 34' is defined in the same way as the DC bias current of transistor 34.

While specific embodiments have been described in detail, those skilled in the art will appreciate that various modifications and alternatives to those details could be developed in light of the overall teachings of the disclosure. For example, the bipolar junction transistors used in the embodiments can be replaced by MOSFETs or junction field effect transistors (JFETs). Accordingly, the particular arrangements disclosed are meant to be illustrative only and not limiting as to the scope of the invention, which is to be given the full breadth of the appended claims and any and all equivalents thereof.

The invention claimed is:

1. An inductive respiration sensor, comprising
an inductive transducer configured to produce a variable inductance when subjected to mechanical deformation;
a transimpedance amplifier having a reference input, a sense input and an output, said sense input being operatively connected to said inductive transducer, said transimpedance amplifier being configured to drive a current from said output into said sense input such that a voltage on said sense input follows a voltage on said reference input and to cause a voltage on said output indicative of said current;
wherein said transimpedance amplifier comprises
a first transistor having a first connection, a second connection and a third connection, said first connection being a collector or drain, said second connection being an emitter or source and said third connection being a base or gate, said first and second connections of said first transistor being operatively connected between said sense input and said output;
a second transistor having a first connection, a second connection and a third connection, said first connection of said second transistor being a collector or drain, said second connection of said second transistor being an emitter or source and said third connection of said second transistor being a base or gate, said second connection of said second transistor being connected to said reference input, said first connection of said second transistor being connected to the third connection of said first transistor, and the third connection of said second transistor being connected to said sense input.

2. The inductive respiration sensor as claimed in claim 1, comprising a coupling capacitor arranged in series with said inductive transducer operatively connected to the sense input.

3. The inductive respiration sensor as claimed in claim 1, comprising a signal generator operatively connected to said reference input, said signal generator being configured to apply an alternating voltage to said reference input.

4. The inductive respiration sensor as claimed claim 3, wherein said signal generator comprises a low-pass filter connected to a digital signal output of a microcontroller.

5. The inductive respiration sensor as claimed in claim 3, comprising a synchronous rectifier operatively connected to said output.

6. The inductive respiration sensor as claimed in claim 3, wherein said signal generator comprises a transistor matched to said second transistor, wherein the emitter or source of said matched transistor is connected with the second connection of said second transistor.

7. The inductive respiration sensor as claimed in claim 1, wherein said transimpedance amplifier, hereinafter termed first transimpedance amplifier, is operatively connected to said inductive transducer at a first terminal thereof,
wherein said inductive respiration sensor comprises a second transimpedance amplifier having a reference input, a sense input and an output, said sense input of said second transimpedance amplifier being operatively connected to said inductive transducer at a second terminal thereof, said second transimpedance amplifier being configured to drive a current from said output of said second transimpedance amplifier into said sense input of said second transimpedance amplifier such that a voltage on said sense input of said second transimpedance amplifier follows a voltage applied to said reference input of said second transimpedance amplifier and to cause a voltage on said output of said second transimpedance amplifier indicative of said current;
wherein said second transimpedance amplifier comprises
a third transistor having a first connection, a second connection and a third connection, said first connection of said third transistor being a collector or drain, said second connection of said third transistor being an emitter or source and said third connection of said third transistor being a base or gate, said first and second connections of said third transistor being operatively connected between said sense input of said second transimpedance amplifier and said output of said second transimpedance amplifier;
a fourth transistor having a first connection, a second connection and a third connection, said first connection of said fourth transistor being a collector or drain, said second connection of said fourth transistor being an emitter or source and said third connection of said fourth transistor being a base or gate, said second connection of said fourth transistor being connected to said reference input of said second transimpedance amplifier, the first connection of said fourth transistor being connected to the third connection of said third transistor, and the third connection of said fourth transistor being connected to said sense input of said second transimpedance amplifier.

8. The inductive respiration sensor as claimed in claim 7, comprising a signal generator operatively connected to said reference input of said first transimpedance amplifier and with opposite polarity to said reference input of said second transimpedance amplifier, said signal generator being configured to generate an alternating voltage difference between said reference inputs of said first and second transimpedance amplifiers.

9. The inductive respiration sensor as claimed in claim 8, wherein said signal generator comprises a low-pass filter connected to a digital signal output of a microcontroller.

10. The inductive respiration sensor as claimed in claim 8, comprising a synchronous rectifier operatively connected to said output of said first transimpedance amplifier and to said output of said second transimpedance amplifier.

11. The inductive respiration sensor as claimed in claim 8, wherein said signal generator comprises a fifth transistor matched to said second transistor and a sixth transistor matched to said fourth transistor, wherein the emitter or source of said fifth transistor is connected with the second connection of said second transistor and wherein the emitter or source of said sixth transistor is connected with the second connection of said fourth transistor.

* * * * *